United States Patent [19]

Prezas et al.

[11] Patent Number: 4,616,659
[45] Date of Patent: Oct. 14, 1986

[54] HEART RATE DETECTION UTILIZING AUTOREGRESSIVE ANALYSIS

[75] Inventors: Dimitrios P. Prezas, Park Ridge; Gustavus H. Zimmerman, III, Westmont, both of Ill.

[73] Assignee: AT&T Bell Laboratories, Murray Hill, N.J.

[21] Appl. No.: 730,486

[22] Filed: May 6, 1985

[51] Int. Cl.$^4$ ............................................. A61B 5/04
[52] U.S. Cl. .................................. 128/706; 128/708; 364/417
[58] Field of Search ............... 128/696, 706, 708, 731; 364/415, 417, 724

[56] References Cited

PUBLICATIONS

"R-Wave Detection in the Presence of Muscle Artifacts", *IEEE Transactions on Biomedical Engineering*, O. Y. De Vel, vol. BME-31, No. 11, pp. 715-717, Nov. 1984.
"Optimal QRS Detector", *Med. & Biol. Eng. & Comput.*, N. V. Thakor, J. G. Webster, and W. J. Tompkins, vol. 21, pp. 343-350, May 1983.
"Estimation of QRS Complex Power Spectra for Design of a QRS Filter", *IEEE Transactions on Biomedical Engineering*, N. V. Thakor, J. G. Webster, and W. J. Tompkins, vol. BME-31, No. 11, pp. 702-705, Nov. 1984.
"Design and Evaluation of QRS and Noise Detectors for Ambulatory E.C.G. Monitors", *Med. & Biol. Eng. & Comput.*, N. V. Thakor and J. G. Webster, vol. 20, pp. 709-714, Nov. 1982.
"Reliable R-Wave Detection from Ambulatory Subjects", *Biomed. Sci. Instrum.*, vol. 14, pp. 67-72, 1978.

*Primary Examiner*—William E. Kamm
*Assistant Examiner*—Mitchell J. Shein
*Attorney, Agent, or Firm*—John C. Moran

[57] ABSTRACT

A system for determining the heart rate in response to an electrocardiogram (EKG) signal that has been filtered by performing an autoregressive analysis, low-pass filtered by performing a digital filtering function, and the rate determined by utilizing a digital peak detection technique. In a heart rate detection system, the EKG signal from an EKG instrument is first digitized and then the colored noise component is removed from the digitized EKG samples by performing a linear predictive coding filtering function on the EKG samples. After the colored noise has been filtered from the digitized EKG samples, a low-pass filtering function is performed to remove high-frequency white noise by utilizing a digital finite impulse response filter. Finally, the heart rate is determined from the previously filtered EKG samples by a peak detection technique that performs a recursive algorithm to determine both the amplitude of the remaining peaks in the EKG samples and the period between these peaks.

14 Claims, 5 Drawing Figures

FIG. 1

FIG. 3
fberg ROUTINE

HEART RATE DETECTION UTILIZING AUTOREGRESSIVE ANALYSIS

CROSS-REFERENCE TO RELATED APPLICATIONS

The following applications were filed concurrently with this application:

C. M. P. Kierney, et al., "Non-Invasive Blood Flow Measurements Utilizing Cardiac Cycle Synchronization", Ser. No. 730,456, and is assigned-in-part to the same assignee as this application; and W. T. Hartwell, et al., "Non-Invasive Blood Flow Measurements Utilizing Autoregressive Analysis With Averaged Reflection Coefficients", Ser. No. 730,487, and is assigned to the same assignee as this application.

TECHNICAL FIELD

This invention pertains to the detection of heart rate. In particular, the invention relates to analyzing electrocardiogram signals (EKG) utilizing autoregressive analysis techniques for eliminating noise and for detecting the heart rate using a digital peak detection technique.

BACKGROUND OF THE INVENTION

The electrocardiogram (EKG) is a commonly monitored vital sign. The QRS complex is the dominant feature of the EKG signal and is used in many clinical instruments such as simple cardiotachometers, arrhythmia monitors, and implantable pacemakers. Under normal conditions, in the absence of muscle artifacts and other electrical noise, a large signal-to-noise ratio prevails and techniques exist for the detection of the QRS complex in particular, R-wave detection. However, in some applications, such as ergonomics, a patient may undergo severe physical stress. The EKG signal will be corrupted with a large non-stationary stochastic muscle artifact signal (EMG) together with extraneous transient and continuous noise components due to electromagnetic interferences. The EMG signal results in color noise being introduced into the EKG signal while 60 Hz electromagnetic interference results in white noise being introduced into the EKG signal. Other electromagnetic interference at higher frequencies will also result in white noise.

In addition, there exists medical techniques which require that the precise start of the cardiac cycle be determined from the EKG signals. One such technique is detailed in the copending application of C. M. P. Kierney, et al. The latter application discloses the utilization of autoregressive analysis techniques for analyzing reflected ultrasonic Doppler shifted signals resulting from the flow of blood cells within internal blood vessels. In Kierney, it is necessary to precisely determine the start and end of each cardiac cycle, so that the Doppler shifted signals for a particular cycle can be divided into a predefined number of time segments so that an autoregressive analysis can be performed on each of these time segments. The start and the end of the cardiac cycles must be precisely determined since the results of the autoregressive analysis are averaged over a plurality of cardiac cycles, and the analysis must be performed at the same relative point in time for each of these cycles.

Therefore, there exists a need for a technique for determining a patient's heart rate from an EKG signal that has various noise artifacts in it. In particular, the need exists for a technique that can reliably and accurately extract the heart rate information from an EKG signal that has been corrupted by both color and white noise.

SUMMARY OF THE INVENTION

In an illustrative method and structural embodiment, a departure in the art is achieved by performing an autoregressive analysis of EKG signals to remove color noise, low-pass digital filtering to remove white noise and determining the heart rate and start of cardiac cycles utilizing a peak detection technique.

Advantageously, a cardiac cycle rate detection system comprises an electrocardiogram (EKG) instrument for obtaining an EKG signal from a patient; and after the EKG signal is digitized by an analog-to-digital converter, a first set of program instructions executed by a computer performs an autoregressive analysis filtering of the EKG digitized samples to remove color noise. A second set of program instructions is responsive to the samples resulting from the autoregressive analysis filtering to perform a digital low-pass filtering on the latter samples to remove high-frequency white noise. Finally, a third set of program instructions is responsive to the samples resulting from the low-pass filtering to determine peaks representing the start of cardiac cycles and from the periodicity of those peaks the cardiac cyclic rate.

Advantageously, the autoregressive analysis filtering is performed by calculating linear filter that model the color noise source causing. Results from the autoregressive analysis filtering are residual samples that represent the difference between the signal predicted by the model and each EKG sample.

In addition, the low-pass filtering is implemented by storing an array of filter coefficients defining the low-pass filter and a set of residual samples from the autoregressive filtering analysis, multiplying the array of coefficients times the set of stored residual samples, and summing the multiplication results. The latter sum equals one output sample of the low-pass filter. Next, the set of stored residual samples is updated by another residual sample replacing a present residual sample, and the multiplication and summing process is repeated to produce another output sample of the low-pass filter.

Advantageously, the third set of program instructions locates the peak of maximum amplitude contained within the low-pass filtered samples and then locates peaks of lesser amplitude that are located further from each other and the peak of maximum amplitude by a distance greater than the number of samples equal to the highest expected heart rate. The instructions then measure the distance between adjacent peaks using as a reference the location of the peak of largest amplitude and test for periodicity by comparing successive distance measurements for substantial equality.

A method for determining the heart rate from signals from an electrocardiogram instrument in the absence of significant color or white noise components performs the following steps: digitizing samples from the electrocardiogram instrument, locating the peak of maximum amplitude, locating peaks of lesser amplitude but at a greater distance from each other than the highest heart rate and having an amplitude greater than a predefined percentage of the peak of largest amplitude, measuring the distance between adjacent peaks, testing for periodicity by comparing successive distance measurements for substantial equality, and displaying the periodicity as an indication of the heart rate.

DETAILED DESCRIPTION

Figure 1:
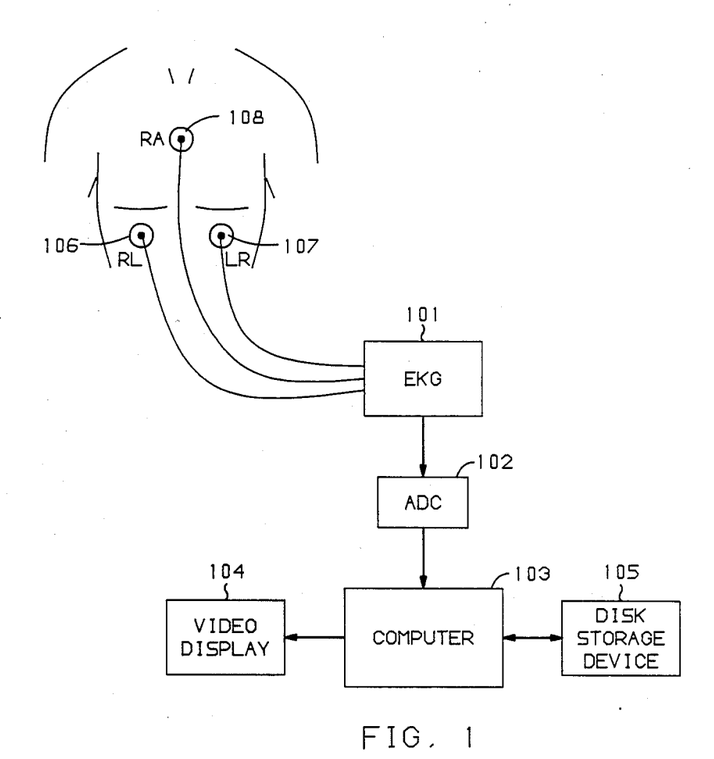
FIG. 1 illustrates, in block diagram form, a blood flow analysis system in accordance with this invention.

A system for analyzing and displaying the heart rate of a patient is illustrated in FIG. 1. EKG 101 is responsive to electrodes 106, 107, and 108 to generate an analog EKG signal containing the QRS complex. This analog EKG signal is first digitized by analog-to-digital converter 102, and then, computer 103 filters and processes the digitized EKG signals and displays the resulting heart rate that is determined from the R-wave of the digitized EKG signal. By executing program instructions, computer 103 first removes the color noise from the data by performing a linear predictive coding (LPC) filtering. This LPC filtering performs the functions of first determining the reflection coefficients which define an inverse filter that models the noise sources and physical structures which have introduced the color noise into the EKG signal. The digitized EKG signals are then filtered by this inverse filter thus removing the color noise. Next, program instructions within computer 103 perform a low pass filtering of the signal resulting from the LPC filtering. Advantageously, this low-pass digital filter can be of the finite impulse response type (FIR). After the LPC and FIR filtering have been performed, computer 103 executes a third set of instructions on the resulting filtered digital signal to determine the position and repetition rate of the R-wave. Once the repetition rate of the R-wave has been determined, it is displayed on video display 104. Advantageously, the resulting information can also be stored on disk storage device 105 for later display.

Figure 2:
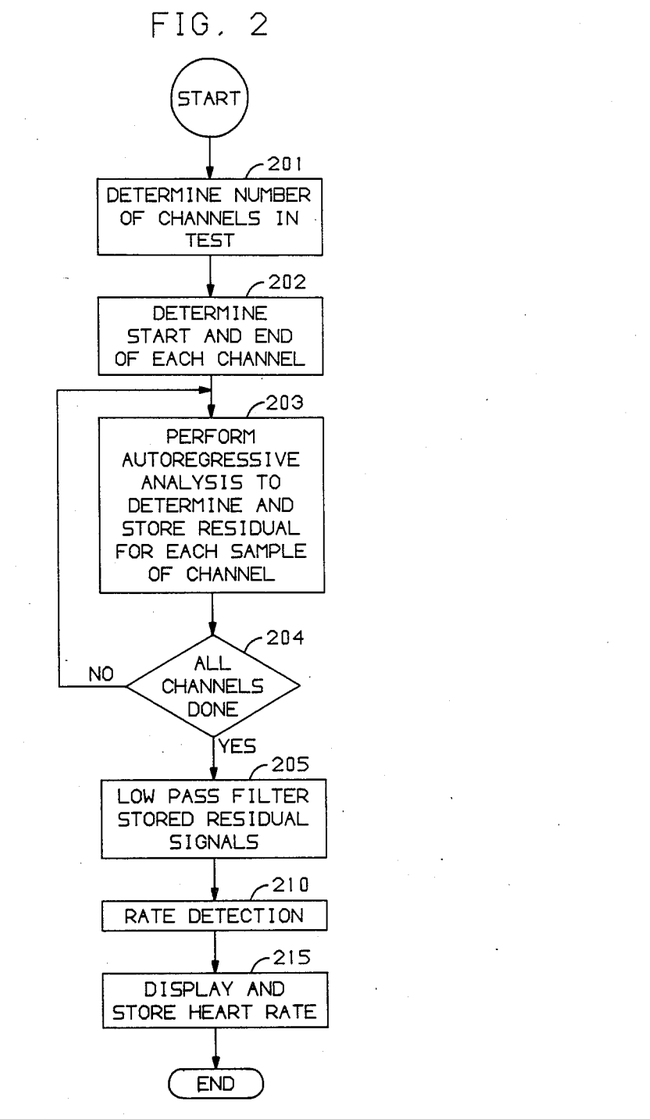
FIG. 2 illustrates, in flowchart form, the programs executed by computer 106 of FIG. 1 in performing the heart rate detection.

FIG. 2 illustrates in greater detail the steps necessary for computer 103 to process the digitized EKG signal received from analog-to-digital converter 102. For each set of EKG samples, block 201 determines the number of time channels or frames that the EKG samples are grouped into by dividing the total number of EKG samples by a predefined number which advantageously may be 50. Once the number of channels has been determined, the start and end of each channel within the EKG samples is then determined by block 202. Blocks 203 and 204 perform a LPC filtering on the digitized EKG samples to remove color noise from these digitized signals. This LPC filtering is accomplished by calculating reflection coefficients that model the sources of the color noise and by processing the digitized EKG samples through this LPC filter. The result of the LPC filtering is commonly called the residual which is the difference or error between each sample and the model specified by the reflection coefficients. Block 203 stores the residual/error for each sample. The LPC filtering performed here is done on the basis of time channels or frames; however, it is well known in the art to perform LPC filtering on a sample-by-sample basis.

Once all the digitized EKG samples have been processed by blocks 203 and 204, the resulting residual samples are low-passed filtered by block 205. This low-pass filter has a bandwidth from 0 to 6 Hz and is implemented with a FIR filter. The impulse response of this FIR filter is a (sin x/X) function.

The low-pass filtering performed by block 205 removes white noise components above 6 Hz and is implemented by doing a digital convolution operation utilizing the previously mentioned function convoluted with the stored residual samples.

Finally, the start of each cardiac cycle and the heart rate is determined by detecting the R-pulse of the QRS complex that is present at the start of each cardiac cycle by block 210; and the results are displayed by block 215. Block 215 also stores the results for later analysis. The R-pulses are detected by implementing a series of operations that first determine the largest pulse present in the data from the FIR filter, next eliminate all samples around this largest pulse by a time equal to the shortest heart beat. Then, other pulses whose amplitudes are greater than 25 percent of the largest pulse are similarly processed. The remaining pulses are removed from the samples. After these remaining pulses have been identified, their periodicity is determined. Greater detail is given later on these operations.

Consider now in greater detail the program illustrated in FIG. 2. The filtering performed by blocks 203 and 204 assumes an filter model given by:

$$E(z) = X(z) F(z) \quad (1)$$

where:
E(z) is the z-transform of the driving or LPC residual signal,
X(z) is the z-transform of the input signal, and
F(z) is an all pole filter.

In the sample domain, equation 1 can be written as follows:

$$e(n) = \sum_{m=0}^{ORDER} fc(m) x(n-m) \quad (2)$$

which can be rewritten as $$e(n) = x(n) - \sum_{m=1}^{ORDER} fc(m) x(n-m) \quad (3)$$

where x(n) represents the present time sample, fc represents filter coefficients, and ORDER represents the number of filter elements.

As described in J. D. Markel and A. H. Gray, "Linear Prediction of Speech", Springer-Verlag, Berlin Herdelberg New York, 1980, on page 10, the driving signal e(n) can be interpreted as the prediction error between the actual data sample x(n) and the linear combination of the previous n samples given by $$\sum_{m=1}^{M} fc(m) x(n-m).$$

Since the driving function term, can be interpreted as an error, the common analysis procedure is to minimize the sum of the squares of this error as a method for determining the filter coefficients. Once, the filter coefficients have been determined, the difference or error that remains at each time sample between the actual data sample x(n) and the results of the modeling is the output signal from the filter.

Many autoregressive techniques have been developed to minimize this error term; and the one utilized here is the Berg Maximum Entropy method which is described in the paper by L. Marple, "A New Autoregressive Spectrum Analysis Algorithm", IEEE Trans. on Acoustics, Speech, and Signal Processing, Vol. ASSP-28, No. 4, August, 1980, pp. 441-454. The Berg method recursively solves for the filter coefficients, fc(m), by using a forward and backward prediction errors. For any given sample point, the error is calculated by considering the sample points in time preceding the sample point under calculations and sample points prior to the particular point under consideration. The forward error is defined by:

$$f_{err}(k) = \sum_{i=0}^{ORDER} fc(i) * x(k - ORDER - i) \quad (4)$$

while the backward error is defined by:

$$b_{err}(k) = \sum_{i=0}^{ORDER} fc(i) * x(k + i) \quad (5)$$

where the values of index k range from 1 to (NPTS-ORDER) and fc(0) is defined as 1. NPTS is the number of sample points in the channel being analyzed. Using these two expressions, the problem is to determine a set of filter coefficients that minimize the sum of both the forward and backward errors summed over all sample points subject to a constraint. Thus, the error to be minimized is given by the following equation:

$$error = \sum_{k=1}^{NPTS-ORDER} f_{err}(k) * f_{err}(k) + b_{err}(k) * b_{err}(k). \quad (6)$$

The constraint on the values of fc is that they satisfy the relation $$fc(k) = FC(k) + rc(ORDER) * FC(ORDER - k) \quad (7)$$

where: $fc(ORDER) = rc(ORDER)$.

where FC represents the coefficients determined when ORDER-1 terms were used in the prediction equation. This relation is called the Levinson recursion, and the term, rc(ORDER), is frequently referred to as the LPC reflection coefficient.

The filter coefficients fc(k) can be solved for in equation 6 by substituting equations 4 and 5 into equation 6 and taking the partial derivative of this equation with respect to fc(ORDER). The resulting equation is a recursive formula given in terms of the reflection coefficient as follows:

$$rc(ORDER) = \frac{-2 \sum_{k=1}^{NPTS-ORDER} b_{err}(k) f_{err}(k + 1)}{\sum_{k=1}^{NPTS-ORDER} ||b_{err}(k)|^2 + |f_{err}(k + 1)|^2|} \quad (8)$$

After the recursive formula in equation 8 has been solved to the desired order of filter, the filtered output of the filter at each sample point is defined by the forward error at that point.

Figure 3:
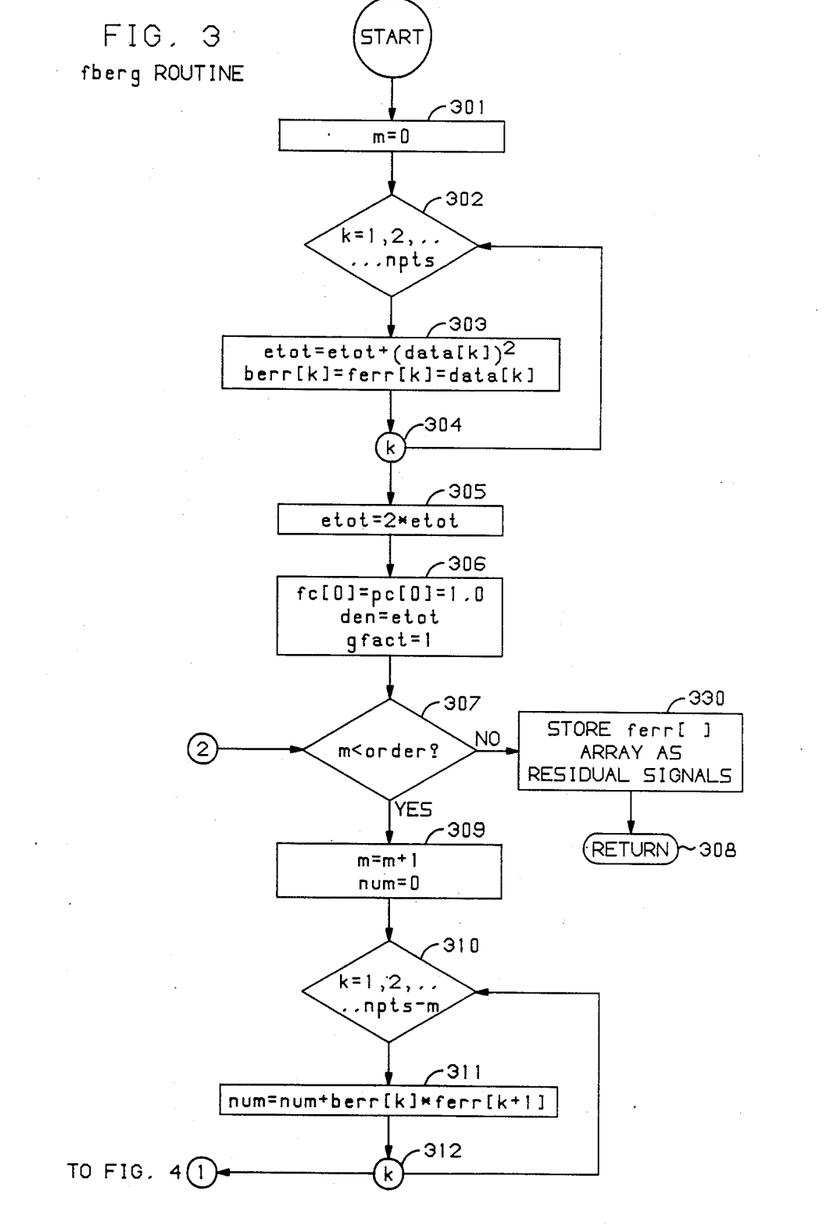
FIGS. 3 and 4 illustrate in greater detail, the program instructions of block 203 of FIG. 2.
Figure 4:
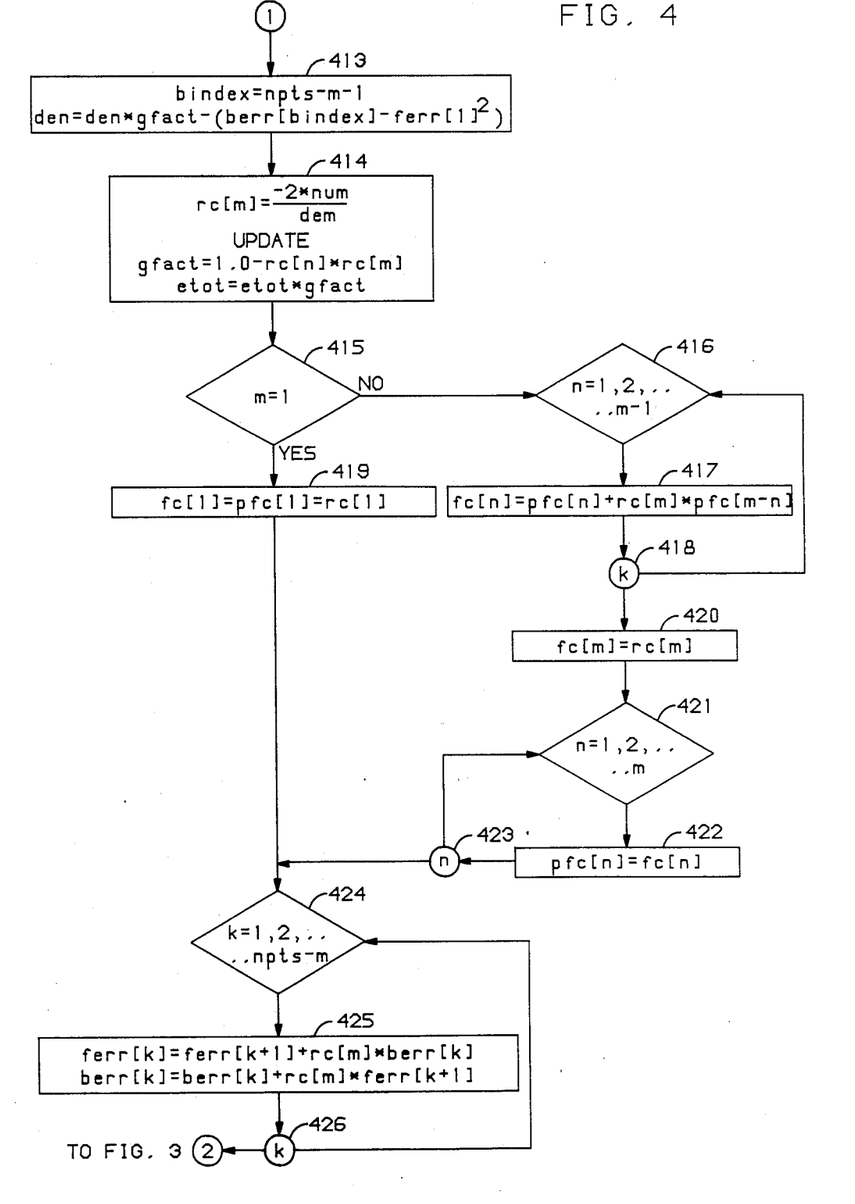

Equation (8) is solved by the fberg routine that is illustrated in FIGS. 3 and 4. This routine calculates equation (8) and verifies that the conditions of equation 7 have been met and implements the Berg method. After the filter has been determined to a sufficient order, the fberg routine defines the values defined by the forward errors as the residual signal, as indicated in block 203.

The fberg routine calculates equation 8 in a recursive manner by first calculating the first reflection filter coefficient for order 1 and then uses this information to calculate a new set of filter coefficients for order 2. Because of this recursive nature, fberg routine is repetitively recalculating equation 8. FIGS. 3 and 4 illustrate the evaluation of equation 8. Blocks 301 through 306, illustrated on FIG. 3, perform the initialization of the various variables used by the subroutine. The initial residual energy, etot, is set equal to the sum of the squares of all the data points of the channel and the backward and forward errors (berr and ferr, respectively) are set equal to corresponding data samples, where the data sample is the digitized Doppler signal. The filter coefficients are initially set equal to 1 by block 306 and the denominator of equation 8 is set equal to the initial residual energy as determined by block 303.

Block 307 determines whether or not the equation has been sufficiently evaluated for the order filter being calculated, and if it has, a return is executed to the program illustrated on FIG. 3 via return block 308. If the filter has not yet been calculated to a sufficient order, then block 309 is executed. The numerator and denominator (num and den, respectively) of equation 8 for this particular order are evaluated by blocks 310 through 313. After the numerator and denominator have been determined, then the reflection coefficient, rc[m], and residual energy for this particular order are evaluated in block 314. Once the reflection coefficient for this order has been determined, then the stepup function is implemented by blocks 315 through 319 to update the previously determined filter coefficients for (ORDER − 1) as defined by the Levinson recursion formula and given in equation 7. The highest order filter coefficient is always equal to the reflection coefficient and is set equal to the reflection coefficient by block 320. The past filter coefficients are then updated by blocks 321 through 323 in order for block 317 to evaluate the next set of filter coefficients. The past filter coefficients are designated as FC(n) in equation 7, and as pfc[n] on FIGS. 3 and 4. The forward and backward errors are next updated by blocks 324 through 326 in order to evaluate blocks 311 and 313 in the next iteration. After the forward and backward errors have been updated, control is passed from block 326 to decision block 307 which determines whether or not all the orders have been evaluated. If all the orders have been evaluated, then the contents of the forward error array are stored by block 530 as the residual signals for this particular channel.

Figure 5:
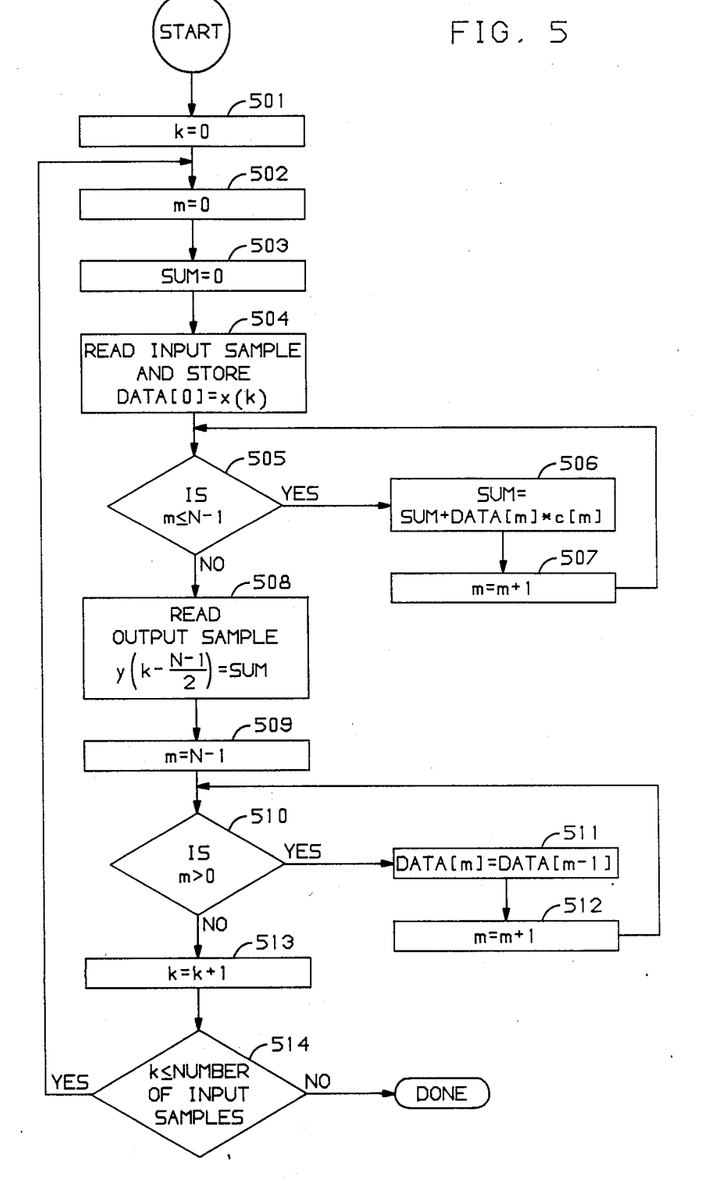
FIG. 5 is a detailed flowchart of block 205 of FIG. 2.

Consider now, in greater detail, the low-pass filtering that is performed by block 205 of FIG. 2 as illustrated in greater detail by a flowchart in FIG. 5. The filter implemented by the flowchart of FIG. 5 is of the FIR type having n stages where n may illustratively be 100. The coefficients for each of these stages are stored in elements of the c[ ] array. The input samples are contained in the x[ ] array, and the output samples are stored in the y[ ] array. The output array is later stored in a file for processing by block 210 of FIG. 2. The values of the filtered coefficients stored in c[ ] can be obtained by using the techniques described in the book entitled, *Digital Signal Processing,* W. D. Stanley, G. R. Dougherty, and R. Dougherty, 1984. The input samples are initially stored in the DATA[ ] array which serves to delay the input signal for latter multiplication by the filter coefficients stored in the c[ ] array. Further, the FIR filter illustrated in FIG. 5 is a linear phase filter.

As illustrated in FIG. 5, blocks 501, 502, and 503 are used to initialize the appropriate variables. As each input sample is read, it is stored in the first element of the DATA[ ] array. The output signal calculations are performed by elements 503, 506, and 507 for all of the elements of the FIR filter. The result of those calculations for each input sample are computed in the variable SUM. The output signal y( ) is delayed by a number corresponding to half the number of filter stages in relation to the input samples x( ) by block 508. Once the output sample has been calculated for an input sample, the data array is updated for the next input sample by blocks 509 through 512. Blocks 513 and 514 control the sequencing of the flowchart shown in FIG. 5 so that all of the input samples are processed. After all of the input samples have been processed, the low-pass filtering function is done and an exit is made from the flowchart illustrated in FIG. 5 under control of block 514.

Consider now in greater detail how block 210 performs the rate detection. The program illustrated in Appendix A is a complete implementation of block 210. The routine first identifies and orders all pulses present in the signal from block 205 in descending order down to pulses that are more than 25 percent of the largest pulse amplitude. In addition, any pulses having an amplitude of less than 25 percent of the largest pulse are removed. As the pulses are found, their position within the test data is recorded. After each pulse has been identified, the routine removes all samples on either side of this largest pulse plus or minus the amount of time of the fastest heart beat which advantageously can be 300 beats/second. Then, the routine scans the test data backward in time from the largest pulse until it finds a second pulse. The routine then proceeds to attempt to go further backward in time by an amount equal to the differences between the largest pulse and the second pulse, plus or minus an error amount that is defined as T which advantageously may be 0.04 seconds. If no pulse is found at this location, it is assumed that the second pulse was a noise pulse. The second pulse is eliminated from the test data and the first step is repeated. However, if a third pulse is found at the point where it was predicted to occur based on the time difference between the largest pulse and the second pulse found, this fact indicates that the second pulse is valid and the program steps backward looking for a fourth pulse at the appropriate place using the same technique as previously described. This procedure is then repeated going forward in time. If going first backwards in time fails, then the process is repeated going first forward in time and assuming that the original set of pulses is available. The resulting pulse amplitudes and their locations found by the previous steps define the starting points of the cardiac cycles of the test results and also the heart rate is defined by periodicity of the pulse locations.

It is to be understood that the above-described embodiment is merely illustrative of the principles of this invention; other arrangements may be devised by those skilled in the art without departing from the spirit and scope of the invention. In particular, one skilled in the art could determine that in the absence of substantial amounts of color and white noise that the peak detection technique alone could be used to detect and display the heart rate.

APPENDIX A

```
#include <stdio.h>
#include <math.h>
#define PMODE 0644
int step,wave;
int SIL;
int a[100],aristera,d[100],dexia,dist,distdd;
int beat;
int F,L,T,k,y;
int counter,i,ss,unv;
int rate,downs,distd;
int fool;
double fooll;
int nelem;
int *r, *nnn;
int am[100],amd[100],amdd[100];
int amz[100],amzd[100],amzdd[100];
int dm[100],dmd[100],dmdd[100];
int puls, pulsd, pulsdd,flag1, flag2, ii, sample;
main(argc,argv)
int argc;
char *argv[];
{
        int search();
        int j,m;
        int pointer1,pointer2,nn[1];
        if(argc == 1){
                printf("-------------------------------------------------\n");
                printf("|                                                |\n");
```

```c
        printf("|    This program gives the peak locations     |\n");
        printf("|    of heart beats in an EKG signal.           |\n");
        printf("|    It also outputs an average heart rate      |\n");
        printf("|    in beats/min every 2 sec.                  |\n");
        printf("|    The program first down-samples the data    |\n");
        printf("|    by -downs-; however, the output of this    |\n");
        printf("|    program gives the true locations in the    |\n");
        printf("|    original sampling rate.                    |\n");
        printf("|                                               |\n");
        printf("|    Usage: beat input Fs downs > output        |\n");
        printf("|                                               |\n");
        printf("|    beat: name of executable file              |\n");
        printf("|    input: name of EKG input file              |\n");
        printf("|    Fs: input sampling rate in Hz              |\n");
        printf("|    downs: downsampling factor (integer)       |\n");
        printf("|    output: name of output file                |\n");
        printf("|                                               |\n");
        printf("|    To compile use:                            |\n");
        printf("|    cc beat.c -lm -i -O -o beat                |\n");
        printf("|                                               |\n");
        printf("|_______________________________________________|\n");
        exit(1);
}
/* Open input and output files */
if((pointer1=open(argv[1],0))== -1)
{
        printf("Cannot open %s\n",argv[1]);
        exit(1);
}
rate=atoi(argv[2]);
downs=atoi(argv[3]);
nelem = 2*rate/downs;
L=nelem;
r = (int*)calloc(nelem,sizeof(int));
nnn = (int*)calloc(nelem,sizeof(int));
dist=0;
/* Define parameters */
counter=1;      /*frame counter*/
wave = 32;
T=wave;                 /*position threshold*/
F=wave; /*freq. threshold*/
SIL=100;
k=1;
m=0;    /*inframe counter*/
sample = 0; /*count number of samples*/
while( read(pointer1,nn,2) == 2 )
{
        sample = sample + 1;
        if (sample%downs == 0)
        {
        m=m+1;
        /*load the signal+ buffer for beat detection*/
        r[m-1]=nn[0];
        if(r[m-1] < 0.0){
                r[m-1]=0.0;
        }
}
        if( m%L == 0)
        {
                /* Do beat detection */
                search();
                /* Write out beat and store last non-zero beat */
                if(counter>2){
        fooll =(double)(rate*60.0)/(double)(distd*downs);
                        fool = fooll;
printf("          beat=%d beats/min.\n",fool);
                        if(distd != 0 ){
```

```
                                        for(i=1;i<=pulsdd;++i){
                                                if(amzdd[i] == 0)
        printf("A peak at location %d\n",((dmdd[i]+1)+(counter-3)*L)*downs);
                                        }
                                }
                                else
                printf ("No periodicity was found for this frame\n");
                        } /*counter>2 */
                        m=0;
                        counter=counter+1;
                                {
                                        distdd=distd;
                                        distd=dist;
                                        for(i=1;i<=pulsd;++i){
                                                amzdd[i] = amzd[i];
                                                amdd[i] = amd[i];
                                                dmdd[i] = dmd[i];
                                        }
                                        pulsdd = pulsd;
                                        for(i=1; i <= puls; ++i){
                                                amzd[i] = amz[i];
                                                amd[i] = am[i];
                                                dmd[i] = dm[i];
                                        }
                                        pulsd = puls;
                                }
                        }
                }
        }
}
int search()
{
        int n,j,M,mleft,mright,s,abs(),new,p;
        int FLEFT,FRIGHT;
        int A[100],D[100],max,min,aa,x,aaa,bbb,general();
        int proj;
        n=1;
        while(n>0){
                a[n]=A[n]=0; /*init max for the frame*/
                for(i=0;i<L;++i){
                        if(r[i]>A[n]){
                                a[n]=A[n]=r[i];
                                d[n]=D[n]=i;
                        }
                }
                if(A[n]==0) break;
                if(A[n]<(A[1]>>2)) break;/*A[1]*0.25*/
                max=D[n]+rate/5; /* max beat rate 300/min; 5 per sec */
                if(max>=L) max=L-1;
                min=D[n]-rate/5;
                if(min<0) min=0;
                for(i=min; i<=max;++i) r[i]=0;
                n=n+1;
        }
        for(i=1;i<n-1;++i){
                for(j=1;j<n-1;++j){
                        if(d[j]>d[j+1]){
                                step=d[j];
                                d[j]=d[j+1];
                                d[j+1]=step;
                                step=a[j];
                                a[j]=a[j+1];
                                a[j+1]=step;
                        }
                }
        }
        for(i=1; i<n; ++i){
                am[i] = a[i];
```

```
                amz[i] = a[i];
                dm[i] = d[i];
        }
        puls = n-1;
        for(i=1;i<n;++i) if(a[i]==A[1]) {
                ss=i;
                break;
        }
        if((n-1)==0) goto noth;
        /*make frame adaptive to the END candidates*/
        for(i=1;i<n;++i){
                if(a[i]!=0){
                        FLEFT=d[i]-T;
                        break;
                }
        }
        for(i=n-1;i>=1;i=i-1){
                if(a[i]!=0){
                        FRIGHT=d[i]+T;
                        break;
                }
        }
        M=0;
left:
        i=ss;
again:
        k=1;
        i=i-1;
        flagl = 0;
        for(ii=1; ii<n; ++ii){
                amz[ii] = am[ii];
        }
        if(i<1){
                mleft=ss;
                goto right;
        }
        aa=d[ss]-d[i];
        p=i-1;
        x=d[i]-aa;
        if(a[i] < ((a[ss]>>1) + (a[ss]>>5) - (a[ss]>>3)) ) goto again;/*a[ss]0.4*/
back:
        if(p<1 || x< FLEFT) {
                mleft=p+1;
                goto rightl;
        }
        if(x>d[p]+T) goto again;
bas:
        step=x-d[p];
        if(abs(step)>T){
                M=0;
                p=p-1;
                if(p<1 || x>d[p]+T) goto again;
                else goto bas;
        }
        y=d[ss]-d[p];
        if (flagl == 0) amz[i] = 0;
        amz[p] = 0;
        flagl = 1;
        M=1;
        k=k+1;
        x=d[p]-aa;
        p=p-1;
        goto back;
rightl:
        new=0;
        p=ss+1;
        x=d[ss]+aa;
```

```
back1:
        if(p>n-1 || x>FRIGHT) {
                if(M==0) goto right;
                else{
                        mright=p-1;
                        goto many;
                }
        }
        if(x<d[p]-T) goto again;
ba:
        step=x-d[p];
        if(abs(step)>T){
                M=0;
                p=p+1;
                if(p>n-1 || x<d[p]-T) goto again;
                else goto ba;
        }
        if(a[p] < ((a[ss]>>1)+(a[ss]>>5)-(a[ss]>>3)) && new==0) goto again;
        new=new+1;
        y=d[p]-d[mleft];
        amz[p] = 0;
        M=1;
        k=k+1;
        x=d[p]+aa;
        p=p+1;
        goto back1;
right:
        i=ss;
againn:
        k=1;
        i=i+1;
        flag2 = 0;
        for(ii=1; i<n; ++i){
                amz[ii] = am[ii];
        }
        if(i>n-1){
                mright=ss;
                goto fin;
        }
        aa=d[i]-d[ss];
        p=i+1;
        x=d[i]+aa;
        if( a[i] < ((a[ss]>>1)+(a[ss]>>5)-(a[ss]>>3)) ) goto againn;
backk:
        if(p>n-1 || x>FRIGHT){
                mright=p-1;
                goto left1;
        }
        if(x<d[p]-T) goto againn;
bass:
        step=x-d[p];
        if(abs(step)>T){
                M=0;
                p=p+1;
                if(p>n-1 || x<d[p]-T) goto
                againn;
                else goto bass;
        }
        y=d[p]-d[ss];
        if (flag2 == 0) amz[i] = 0;
        amz[p] = 0;
        flag2 = 1;
        M=1;
        k=k+1;
        x=d[p]+aa;
        p=p+1;
        goto backk;
```

```
leftl:
        new=0;
        p=ss-1;
        x=d[ss]-aa;
backkl:
        if(p<1 || x< FLEFT){
                if(M==0) goto fin;
                else{
                        mleft=p+1;
                        goto many;
                }
        }
        if(x>d[p]+T) goto againn;
basss:
        step=x-d[p];
        if(abs(step)>T){
                M=0;
                p=p-1;
                if(p<1 || x>d[p]+T) goto
                againn;
                else goto basss;
        }
        if(a[p] < ((a[ss]>>1)+(a[ss]>>5)-(a[ss]>>3)) && new==0) goto againn;
        new=new+1;
        y=d[mright]-d[p];
        M=1;
        k=k+1;
        x=d[p]-aa;
        p=p-1;
        goto backkl;
fin:
        s=1;
saxla:
        s=s+1;
        if(s>n-1) goto one;
        aa=d[ss]-D[s];
        if(aa<0) aa= -aa;
        if(d[ss]>D[s]){
                aaa=d[ss]+aa;
                bbb=D[s]-aa;
                mright=ss;
                for(i=1;i<n;++i) if(d[i]==D[s]) {
                        mleft=i;
                        break;
                }
                goto common;
        }
        aaa=D[s]+aa;
        bbb=d[ss]-aa;
        for(i=1;i<n;++i) if(d[i]==D[s]) {
                mright=i;
                break;
        }
        mleft=ss;
common:
        y=d[mright]-d[mleft];
        step=y-dist;
        if(step<0) step= -step;
        if(dist!=0 && step>F) goto saxla;
        /*for secondary pulses in case of two*/
        /* Use variable END point on the LEFT to accommodate    */
        /* start-up voiced--do it only if previous is no-beat */
        if(dist==0){
                if(aaa<(L-T) || bbb>=(FLEFT+(T<<1))){
                        goto saxla;
                }
```

```
            }
    else    {
            if(aaa<L-T || bbb>=T){
                    goto saxla;
            }
    }
    if(A[s] < ((a[ss]>>1)+(a[ss]>>5)-(a[ss]>>3)) ) goto saxla;
    k=1;
    goto many;
noth:.
    k=1;
    dist=general();
    beat=0;
    goto returna;
     if(counter!=1){
            aristera=d[ss];
            dist=general();
    }
    beat=d[ss]-dexia+L;
    dexia=d[ss];
    amz[ss] = 0;
    goto returna;
many:
    if(counter!=1) {
            aristera=d[mleft];
            dist=general();
    }
    dexia=d[mright];
    beat=y/k;
    amz[ss] = 0;
    amz[mleft] = 0;
    amz[mright] = 0;
returna:
    if(counter==1) distd=dist;
    if(counter==2) {
            distdd=distd;
            distd=dist;
    }
    if(counter>2){
            if(distdd==0 && dist==0) if(distd!=0) distd=0;
            if(distdd!=0 && dist!=0) if(distd==0) {
                    step=dist-distdd;
                    if(abs(step)<(F<<1)) distd=(distdd+dist)>>1;
            }
    }
}
int general(){
    int gen;
    if(dist==0){
            unv=1;
            step=dexia+beat-aristera-L;
            if(L-dexia+aristera<30 ) step=step-y/k;/*for split pulse*/
            if(step<0) step= -step;
            if(step<=T+2) goto bbeat;
            else goto nobeat;
    }
    if(unv==0){
            step=dexia+beat-aristera-L;
            if(L-dexia+aristera<30 ) step=step-y/k;
            if(step<0) step= -step;
            if(step<=T+2)goto next;
            else goto nobeat;
    }
```

```
next:
          step=abs(beat-dist);
          if(step<=F) goto bbeat;
          step=abs((beat<<1) -dist);
          if(distdd!=0){
                    if(step<=(beat>>1)) goto raise;
                    else goto nobeat;
          }
          else{
                    if(step<=T){
                              if(abs(beat-y/k)>F) goto raise;
                              else goto bbeat;
                    }
                    else goto nobeat;
          }
raise:
          beat=distd;
bbeat:
          if(beat<32 || beat>L) goto nobeat;
          if(a[ss]<SIL) goto nobeat;
          gen=beat;
          unv=unv-1;
          return(gen);
nobeat:
          gen=0;
          return(gen);
}
```

What is claimed is:

1. A detection system for determining the cardiac cyclic rate by detecting a predetermined component of the cardiac cycle, comprising:
   means for obtaining cardiac signals defining a plurality of cardiac cycles;
   means for performing an autoregressive analysis filtering of said cardiac signals to remove color noise;
   means for executing a low-pass filtering of the autoregressive filtered signals to remove white noise;
   means for peak detecting the low-pass filtered signals to detect said predetermined component thereby determining said cyclic rate; and
   means for displaying said cyclic rate in response to the detection of each predetermined component.

2. The system of claim 1 wherein said predetermined component is the R-peak of the QRS complex of said cardiac cycle.

3. The system of claim 1 wherein said performing means comprises:
   means from calculating linear filter coefficients for said cardiac signals modeling the source producing said color noise;
   means responsive to said linear filter coefficients and said cardiac signals for computing a plurality of residual signals representing the difference between the model defined by said linear filter coefficients and each of said cardiac signals with said residual signals representing the results of said autoregressive analysis filtering.

4. The system of claim 3 wherein said calculating means comprises:
   means for dividing said cardiac signals into a plurality of channels each having a predefined number of cardiac signals;
   means for computing reflection coefficients for each of said channels; and
   means for stepping-up said reflection coefficients to obtain said linear filter coefficients for each of said channels.

5. The system of claim 4 wherein said obtaining means comprises means responsive to patient electrocardiogram signals for generating said cardiac signals.

6. The system of claim 5 wherein said executing means comprises:
   means for storing a plurality of filter coefficients defining the low-pass filter;
   means for storing a set of said autoregressive filtered signals;
   means for multiplying said filter coefficients times said stored set of autoregressive filtered signals;
   means for summing the results of each of said multiplication; and
   means for generating one of said low-pass filtered signals from said summed results.

7. The system of claim 6 wherein said executing further comprises means for discarding one of said stored set of said autoregressive filtered signals;
   means for storing another autoregressive filtered signal in said stored set of said autoregressive filtered signals; and
   means for activating said multiplying, summing, and generating means to produce another one of said low-pass filtered signals.

8. The system of claim 7 wherein said peak detecting means comprises:
   means for locating the main R-peak of maximum amplitude within said low-pass filtered signals;
   means for locating peaks of lesser amplitude than that of said maximum amplitude spaced by not less than a minimum distance based on the highest expected heart rate from said peak of maximum amplitude and from each other within said low-pass filtered signals;
   means for measuring one-by-one the distances between adjacent peaks using as a reference the location of said peak of maximum amplitude;

means for testing for periodicity by comparing successive distance measurements for substantial equality and rejecting peaks which are not periodically related to the peak of maximum amplitude; and means for determining said heart rate from the periodicity.

9. The system of claim 8 wherein said locating means for peaks of lesser amplitude further comprises means for ordering peaks of acceptable amplitude by time of occurrence within said low-pass filtered signals rather than by amplitude.

10. The system of claim 8 wherein said distance-measuring means comprises means for measuring first the separation distance of a given peak from the main peak and then comparing the location of given peaks with assumed locations separated from the main peak by multiples of said separating distance, failure to match within a preselected tolerance the location of actual peaks with said assumed locations being an indication of lack of periodicity of such other peak with said main peak.

11. A system for determining heart beat rate by detecting the R-wave of the QRS complex of a patient's electrocardiogram signal, comprising:

means for obtaining said patient's electrocardiogram signals;

means for digitizing said electrocardiogram signals;

means for dividing said digitized electrocardiogram signals into a plurality of channels each having a predefined number of electrocardiogram signals;

means for computing reflection coefficients for each of said channels from said digitized electrocardiogram signals modeling noise contained within said electrocardiogram signals;

means for computing the residual representing the difference between said model and said electrocardiogram signals from said residual thereby representing the linear filtered output signals of said model;

means for storing a plurality of filtered coefficients defining a low-pass filter;

means for computing output signals of said low-pass filter in response to said linear filtered signals and said stored filtered coefficients;

means for locating the main R-peak of maximum amplitude within the low-pass filtered signals;

means for locating peaks of lesser amplitude than that of said peak of maximum amplitude by not less than a minimum distance based on the highest expected heart rate from said peak of maximum amplitude and from each other within said low-pass filtered signals;

means for measuring one-by-one the distances between adjacent peaks using as a reference the location of said peak of said maximum amplitude;

means for testing for periodicity by comparing successive distance measurements for substantial equality and rejecting peaks which are not periodically related to the peak of maximum amplitude; and means for determining said heart rate from the periodicity.

12. A monitoring method for determining the cardiac cycle rate by detecting a predetermined component of the cardiac cycle, comprising:

reading the electrocardiogram signals of a patient for a plurality of cardiac cycles;

performing an autoregressive analysis filtering of said electrocardiogram signals to remove color noise;

removing white noise by low-pass filtering said autoregressive filtered signals;

locating the main peak of maximum amplitude within the low-pass filtered signals;

locating the main peak of maximum amplitude within the low-pass filtered signals;

locating peaks of lesser amplitude than said peak of maximum amplitude by not less than a minimum distance based on the highest expected heart rate from said peak of maximum amplitude and from each other within said low-pass filtered signals;

measuring the distance between adjacent peaks using as a reference the location of said peak of maximum amplitude;

testing for periodicity by comparing successive distance measurements for substantial equality and rejecting peaks which are not periodically related to the peak of maximum amplitude; and determining said cardiac cycle rate from the periodicity.

13. The method of claim 12 wherein said performing step comprises regressively executing the following steps:

computing a forward error signal for each of said electrocardiogram signals representing the difference between each electrocardiogram signals and succeeding electrocardiogram signals;

computing a backward error signal representing the difference between each of said electrocardiogram signals and preceding electrocardiogram signals;

recursively computing reflection coefficients from said forward and backward error signals; and setting said autoregressive filtered signals equal to said forward error signals of all of said electrocardiogram signals.

14. A method for measuring the heart rate of a patient in response to an electrocardiogram signal comprising the steps of:

digitizing samples of said electrocardiogram signal;

locating the peak of maximum amplitude in said digitized samples;

locating peaks of lesser amplitude spaced a distance apart greater than the highest expected heart rate and having an amplitude greater than a predefined percentage of said peak of largest amplitude;

measuring the distance between adjacent peaks;

testing for periodicity by comparing successive distance measurements for substantial equality; and displaying the periodicity as an indication of said heart rate.

* * * * *